(12) United States Patent
Hahn et al.

(10) Patent No.: US 6,747,122 B2
(45) Date of Patent: Jun. 8, 2004

(54) PROCESS FOR THE PREPARATION OF POLYMERIC SULFUR COMPOUNDS

(75) Inventors: Josef Hahn, Köln (DE); Marco Runk, Brühl (DE); Hermann-Josef Weidenhaupt, Pulheim (DE); Hartmuth Buding, Titz (DE)

(73) Assignee: Bayer Aktiengesellschaft, Leverkusen (DE)

( * ) Notice: Subject to any disclaimer, the term of this patent is extended or adjusted under 35 U.S.C. 154(b) by 54 days.

(21) Appl. No.: 10/197,362

(22) Filed: Jul. 15, 2002

(65) Prior Publication Data

US 2003/0100703 A1 May 29, 2003

(30) Foreign Application Priority Data

Jul. 20, 2001 (DE) .......................... 101 34 686

(51) Int. Cl.$^7$ .......................... C08G 75/00; C08G 75/14
(52) U.S. Cl. ...................... 528/387; 528/373; 528/389; 528/486; 528/492
(58) Field of Search ................. 528/387, 373, 528/389, 486, 492

(56) References Cited

U.S. PATENT DOCUMENTS

| | | | |
|---|---|---|---|
| 2,989,513 A | 6/1961 | Hendry et al. ................. | 260/79 |
| 3,523,926 A | 8/1970 | Mirviss ........................ | 260/79 |
| 4,147,640 A | 4/1979 | Jayne et al. ................... | 252/45 |
| 4,739,036 A | 4/1988 | Colvin et al. ................ | 528/389 |
| 4,792,589 A | 12/1988 | Colvin et al. ................ | 525/343 |
| 4,902,775 A | 2/1990 | Colvin et al. ................ | 528/389 |
| 2001/0029290 A1 | 10/2001 | Weidenhaupt et al. ...... | 528/374 |

FOREIGN PATENT DOCUMENTS

EP 0 258 168 3/1988

OTHER PUBLICATIONS

Colvin H et al: "Schwefe/Olefin–Copolymere Als Vulkanisationsmittel Fuer Kautschuk" Gummi.

Fasern, Kunststoffe. Internationale Fachzeitschrift Fur Die Polymer–Verarbeitung, Gentner Verlag. Stuttgart, DE, Bd. 50, Nr. 8, Aug. 1, 1997, Seiten 627–634, XP000697954 ISSN: 0176–1625 Seite 628, Spalte 2, Absatze 1, 2; Abbildung 1 Seite 631, Spalte 1, Absatz 3—Spalte 2, Absatz 2; Abbildungen 3–5; Tabelle 2.

*Primary Examiner*—Duc Truong
(74) *Attorney, Agent, or Firm*—Joseph C. Gil; Jennifer R. Seng

(57) ABSTRACT

The invention relates to a simple process for the preparation of polymeric sulfur compounds with polythiocyclopentanediyl structural elements which are used as vulcanizing agents for diene rubbers.

7 Claims, No Drawings

PROCESS FOR THE PREPARATION OF POLYMERIC SULFUR COMPOUNDS

FIELD OF THE INVENTION

The invention relates to a process for the preparation of polymeric sulfur compounds with polythiocyclopentanediyl structural units which are used as vulcanizing agents for diene rubbers.

BACKGROUND OF THE INVENTION

EP-A 258 168 discloses the reaction of olefins with sulfur in water, it being possible for bases to be present as catalysts. Cyclopentadiene and dicyclopentadiene, inter alia, are mentioned as preferred olefins (page 4, lines 14–15). Cyclopentadiene de facto does not occur in the examples according to the present invention. Regarding industrial applicability, it is disclosed on page 7, lines 57–58 and page 8, lines 1–3 that the vulcanizing agents according to the invention lead to vulcanizates which are comparable in their physical properties to the properties obtained with a conventional sulfur vulcanization system. An improved reversion stability of the vulcanizates according to the present invention is not described. In example 1 of the German patent application with the application number DE 100002878.0, it is shown that the products cited therein from dicyclopentadiene and sulfur do not give vulcanizates with improved reversion stability.

U.S. Pat. No. 3,523,926 discloses vulcanizing agents from diolefins, such as e.g. cyclopentadiene and dicyclopentadiene, and sulfur with amines as the catalyst. The additional use of hydrogen sulfide is neither described nor suggested in this reference.

U.S. Pat. No. 2,989,513 discloses polymers of sulfur and an olefin for vulcanization of rubber. In column 3, line 21, cyclopentadiene, inter alia, is mentioned as a useful olefin. The reaction according to this reference is preferably carried out at between 145° and 160° C. The embodiment examples include only copolymers of sulfur and styrene or sulfur and ethylene or isobutylene. At no point in this reference is the additional use of hydrogen sulfide described or suggested.

The German patent application with the application number DE 100002878.0 already describes polymeric sulfur compounds with polythiocyclopentanediyl structural elements which can be employed as crosslinking agents for diene rubbers. According to DE 100002878.0, the polymeric sulfur compounds are obtained by reaction of di-cyclopentenylpolysulfanes, which are known per se, with sulfur and hydrogen sulfide in the presence of amines at temperatures in the range from approx. 100° to 180° C. The di-cyclopentenylpolysulfanes employed can be prepared by (a) addition of sulfanes on to cyclopentadiene and/or methylcyclopentadiene or by (b) reaction of the cyclopentadienes according to the invention with liquid hydrogen sulfide to give (methyl)cyclopent-2-ene-1-thiol and subsequent reaction with elemental sulfur in the presence of amines as a catalyst. In the process according to (a), the preparation and handling of the sulfanes is very complex and expensive from the safety point of view, since sulfanes can decompose spontaneously into hydrogen sulfide and sulfur in contact with rough surfaces. In the process according to (b) the handling of a large amount of liquid hydrogen sulfide is necessary, which requires a gas liquefaction plant. Furthermore, the processes according to (a) and (b) are multi-stage processes.

SUMMARY OF THE INVENTION

The object of the present invention was to provide a one-stage process for the preparation of polymeric sulfur compounds with polythiocyclopentanediyl structural units which is industrially simple and easy to realize.

The object has been achieved by direct reaction of (methyl)cyclopentadiene with sulfur and hydrogen sulfide in the presence of a catalyst.

Therefore, the invention provides a process for the preparation of polymeric sulfur compounds of the formula

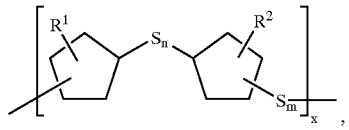

wherein the substituents $R^1$ and $R^2$ are identical or different and represent hydrogen or methyl, n and m denote integers in the range from 2 to 12, and x denotes an integer in the range from 2 to 500, wherein (methyl)cyclopentadiene is reacted with sulfur and hydrogen sulfide at 100° to 180° C., in the presence of a catalyst, the molar ratio of sulfur to hydrogen sulfide being 1:0.1 to 1:5, and the molar ratio of (methyl)cyclopentadiene to sulfur being 1:1 to 1:9.

DETAILED DESCRIPTION OF THE INVENTION

Therefore, the present invention provides a process for the preparation of polymeric sulfur compounds of the formula

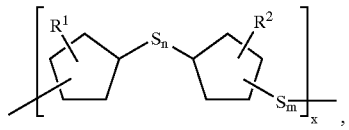

wherein the substituents $R^1$ and $R^2$ are identical or different and represent hydrogen or methyl, n and m denote integers in the range from 2 to 12, preferably 2 to 7, and x denotes an integer in the range from 2 to 500, preferably 2 to 300, in particular 2 to 100, wherein (methyl)cyclopentadiene is reacted with sulfur and hydrogen sulfide at 100° to 180° C., preferably at 130° to 150° C., in the presence of a catalyst, the molar ratio of sulfur to hydrogen sulfide being 1:0.1 to 1:5, preferably 1:0.5 to 1:2, and the molar ratio of (methyl)cyclopentadiene to sulfur being 1:1 to 1:9, preferably 1:2 to 1:5.

The numbers of the sulfur atoms n and m in the polymer chain are of course, in each case integers. Fractions can also result for the sulfur chain length averaged over all the polymer molecules, due to the formation of a mean value.

The number x for the recurring unit in a specific polymer molecule is an integer. Fractions can also result for the average recurring unit of the total number of polymers, due to the formation of a mean value.

Brönsted acids, Lewis acids or amines are possible as the catalyst for the process according to the present invention. Phosphoric acid, perchloric acid or trifluoromethanesulfonic acid or also mixtures thereof are preferably employed as Brönsted acids. Anhydrous aluminum chloride and in particular, boron trifluoride-etherate are preferably employed as Lewis acids. Possible amines are primary, secondary or tertiary, aliphatic, cycloaliphatic or aromatic or heterocyclic amines or mixtures thereof. Secondary or tertiary aliphatic amines with $C_1$- to $C_4$-alkyl radicals, such as e.g. dimethylamine, diethylamine, di-n-propylamine, di-i-propylamine, di-n-butylamine, trimethylamine, triethylamine, tri-n-propylamine, tri-i-propylamine or tri-n-butylamine are preferably employed. Triethylamine is more preferred. The catalyst is, in general, employed in an amount of 0.001 to 10 parts by wt., preferably 0.1 to 5 parts by wt., based on 100 parts by wt. of sulfur.

The reaction according to the present invention takes place under pressure, this usually establishing itself in a range from approx. 1 to 500 bar, preferably approx. 1 to 250 bar, depending on the nature of the starting substances and the amount thereof and depending on the temperature used.

The process according to the present invention can be carried out e.g. by a discontinuous or continuous process. In the discontinuous process (methyl)cyclopentadiene is initially introduced into a pressure reactor together with sulfur, hydrogen sulfide and the catalyst and the mixture is then heated up to a temperature of 100° to 180° C., while stirring, and reacted, or (methyl)cyclopentadiene is pumped into the stirred mixture which has been heated up to the temperature according to the invention (feed process). In the continuous process the educts can be added to the reactor individually or also as a mixture and reacted at the reaction temperatures according to the invention.

In an embodiment of the present invention, sulfur, hydrogen sulfide and the catalyst are initially introduced into an autoclave and the (methyl)cyclopentadiene is then added at the reaction temperature according to the present invention (feed process).

The reaction according to the present invention can also be carried out in solvent. Possible suitable solvents are aliphatic $C_5$- to $C_{12}$-hydrocarbons, such as e.g. pentane, hexane, heptane or octane, or corresponding hydrocarbon mixtures, such as e.g. petroleum ether with a boiling point of 40° to 70° C., light petroleum with a boiling point of 70° to 90° C. or middle petroleum with a boiling point of 90° to 180° C., $C_5$- to $C_{10}$-cycloalkanes, such as e.g. cyclopentane, methylcyclopentane, cyclohexane, methylcyclohexane, cycloheptane or decalin, or corresponding mixtures thereof, $C_1$- to $C_5$-halogenoalkanes, such as e.g. chloromethanes, fluorochloromethanes, fluorochloroethanes or tetrachloroethylene, or corresponding mixtures thereof, $C_1$- to $C_5$-alcohols, such as e.g. methanol, ethanol, n- and i-propanol and n-, i- and tert-butanol, or corresponding mixtures thereof, ethers, such as e.g. diethyl ether, methyl tert-butyl ether or tetrahydrofuran, or corresponding ether mixtures thereof, and (chloro)aromatics, such as e.g. benzene, toluene xylene or chlorobenzene, and mixtures thereof. The solvents mentioned can, of course, also be employed in any desired mixtures with one another. Preferred solvents are toluene, methanol, hexane, petroleum ether or light petroleum. The amount of solvent is approx. 1 to 300 parts by wt., preferably approx. 1 to 150 parts by wt., based on 100 parts by wt. of (methyl)cyclopentadiene.

In an embodiment of the present invention, the reaction is carried out without a solvent.

The reaction time is about 0.5 to 10 h, preferably about 3 to 6 h. Excess hydrogen sulfide is removed from the reaction mixture and any solvent employed is distilled off.

EXAMPLES

Example

Feed process

A 1.3 l stirred autoclave which had been rendered inert with nitrogen was charged with 139.7 g (4.36 mol) sulfur, 2.4 g triethylamine and 180.0 g (5.28 mol) hydrogen sulfide. The autoclave was heated to 140° C., while stirring. At this temperature, the autoclave had an internal pressure of approx. 70 bar. 96.0 g (1.45 mol) of freshly distilled cyclopentadiene were pumped into this mixture in the course of approx. 9 minutes. After a reaction time of 4 h, calculated from the end of the feeding-in, the internal pressure in the reactor had fallen to approx. 35 bar. The autoclave was cooled, let down and flushed with nitrogen. A yellow, plastic solid which was completely soluble in carbon disulfide was obtained as the reaction product. The reaction proceeded virtually quantitatively.

The following analytical data were obtained:

$(C_{10}H_{16}S_{7.5})_x$ (MW: $[376.69]_x$)

C calc.: 31.89% H calc.: 4.28% S calc.: 63.83%

C found: 31.7% H found: 4.3% S found: 63.8%

IR (KBr): $\nu$=1437 1/cm (s)

$\nu$=1313 1/cm (m)

$\nu$=1240 1/cm (s)

DSC: Glass transition temperature $T_g$=−14.3° C. mid point (rate of heating up: 5° C./min)

GPC: A mixture of chloroform and carbon disulfide (volume ratio 10:1) was employed as the solvent for the reaction product.

The insoluble content of approx. 50 parts by wt., based on 100 parts by wt. of reaction product to be dissolved, was separated off.

x=2 to 85 (Column: Jordi Gel DVB, 500 Å, 500×10 mm, eluent: chloroform with 0.5 part by wt. ethanol, UV detection: 260 nm, retention time: 9.7 to 23 min)

NMR: $^1$H- and $^{13}$C-NMR ($CDCl_3/CS_2$=10:1; volume ratio)

The typical ranges of the chemical shift (ppm) for 1,2-substitution are:

1,2-substituted $$\left[ S_n \underset{5\;4\;3}{\overset{1\;2}{\diagup\!\!\diagdown}} S_m \right]_x$$

| Atom no. | δ ($^1$H) | δ ($^{13}$C) |
|---|---|---|
| 1, 2 | 3.5–4.1 | 54.1–58.5 |
| 3, 5 | 1.9–2.4 | 30.7–34.1 |
| 4 | 1.5–1.9 | 21.8–24.6 |

The typical ranges of the chemical shift (ppm) for 1,3-substitution are:

1,3-substituted $$\left[ S_n \underset{5\;4}{\overset{2}{\diagup 1\;3\diagdown}} S_m \right]_y$$

| Atom no. | δ ($^1$H) | δ ($^{13}$C) |
|---|---|---|
| 1, 3 | 3.2–3.9 | 48.1–51.7 |
| 2 | 2.2–2.4 | 37.9–41.7 |
| 4, 5 | 1.8–2.4 | 30.7–34.1 |

Content of the 1,3-substituted structure in the polymer: approx. 50%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of polymeric sulfur compounds of the formula

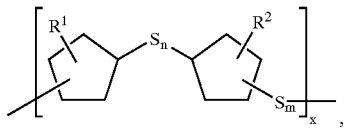

wherein the substituents
  $R^1$ and $R^2$ are identical or different and represent hydrogen or methyl,
  n and m denote integers in the range from 2 to 12 and
  x denotes an integer in the range from 2 to 500, comprising the step of reacting (methyl)cyclopentadiene with sulfur and hydrogen sulfide at 100° to 180° C. in the presence of a catalyst, the molar ratio of sulfur to hydrogen sulfide being 1:0.1 to 1:5 and the molar ratio of (methyl)cyclopentadiene to sulfur being 1:1 to 1:9.

2. A process according to claim 1, wherein said catalyst is selected from the group consisting of Brönsted acids, Lewis acids or amines.

3. A process according to claim 1, wherein n and m denote integers in the range of 2 to 7.

4. A process according to claim 1, wherein x denotes an integer from 2 to 300.

5. A process according to claim 4, wherein x denotes an integer from 2 to 100.

6. A process according to claim 1, wherein the molar ratio of sulfur to hydrogen sulfide is 1:0.5 to 1:2.

7. A process according to claim 1, wherein the molar ratio of (methyl)cyclopentadiene to sulfur is 1:2 to 1:5.

* * * * *